(12) United States Patent
Hidaka et al.

(10) Patent No.: US 6,495,724 B1
(45) Date of Patent: *Dec. 17, 2002

(54) CATALYSTS FOR PRODUCING METHYLAMINES AND METHOD FOR MANUFACTURING THE SAME

(75) Inventors: Toshio Hidaka, Tsukuba (JP); Katsumi Higuchi, Tsukuba (JP); Takeshi Kawai, Tsukuba (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/559,751

(22) Filed: Apr. 27, 2000

Related U.S. Application Data

(62) Division of application No. 09/418,605, filed on Oct. 15, 1999, now abandoned.

(30) Foreign Application Priority Data

Oct. 15, 1998 (JP) .......................................... 10-293772

(51) Int. Cl.⁷ ............................................ C07C 209/64
(52) U.S. Cl. ...................................................... 564/486
(58) Field of Search .................................. 564/479, 486

(56) References Cited

U.S. PATENT DOCUMENTS

| | | | |
|---|---|---|---|
| 4,082,805 A | 4/1978 | Kaeding | |
| 4,205,012 A | 5/1980 | Parker et al. | |
| 4,313,003 A | 1/1982 | Weigert | |
| 4,436,938 A | 3/1984 | Tompsett | |
| 4,440,871 A | * 4/1984 | Lok et al. | 502/214 |
| 4,681,864 A | 7/1987 | Edwards et al. | 502/63 |
| 4,874,896 A | * 10/1989 | Olsen et al. | 564/479 |
| 5,087,347 A | 2/1992 | Miller | 208/46 |
| 5,248,647 A | 9/1993 | Barger | 502/214 |
| 5,324,493 A | 6/1994 | Mueller et al. | 423/311 |
| 5,648,058 A | 7/1997 | Balkus, Jr. et al. | 423/702 |
| 5,663,471 A | 9/1997 | Kvisle et al. | |
| 5,741,751 A | 4/1998 | Miller | 502/208 |
| 6,153,798 A | * 11/2000 | Hidaka et al. | 564/479 |
| 6,180,828 B1 | * 1/2001 | Hidaka et al. | 564/479 |

FOREIGN PATENT DOCUMENTS

| | | |
|---|---|---|
| EP | 0 025 693 | 3/1981 |
| EP | 0 025 693 A1 | 3/1981 |
| EP | 0 210 718 | 2/1987 |
| EP | 0 210 718 A1 | 2/1987 |
| EP | 0 324 267 | 7/1989 |
| EP | 0 324 267 A1 | 7/1989 |
| EP | 0 893 159 | 1/1999 |
| EP | 0 893 159 A1 | 1/1999 |
| JP | 54-148708 | 11/1979 |
| JP | 56-46846 | 4/1981 |
| JP | 56-69846 | 6/1981 |
| JP | 56-113747 | 9/1981 |
| JP | 58-49340 | 3/1983 |
| JP | 59-210050 | 11/1984 |
| JP | 59-227841 | 12/1984 |
| JP | 61-254256 | 11/1986 |
| JP | 2-734 | 1/1990 |
| JP | 9-197232 | 7/1997 |
| JP | 10-25832 | 1/1998 |
| JP | 11-35527 | 2/1999 |

OTHER PUBLICATIONS

Dahl, et al., "The effect of crystallite size on the activity and selectivity of the reaction of ethanol and 2–propanol over SAPO–34", Microporous Mesoporous Materials, vol. 29, Jun. 1999, pp. 159–171.

JP 58–49340 A, Isao Mochida, Mar. 23, 1983.

JP 59–210050 A, Yoshirou Ashina, Nov. 28, 1984.

JP 59–227841 A, Yoshirou Ashina, Dec. 21, 1984.

Dahl et al., *"The effect of crystallite size on the activity and selectivity of the reaction of ethanol and 2–propanol over SAPO–34"*, Microporous and Mesoporous Materials, 29 (1999), pp. 159–171.

* cited by examiner

*Primary Examiner*—Brian J. Davis
(74) *Attorney, Agent, or Firm*—Fitch, Even, Tabin & Flannery

(57) ABSTRACT

Catalysts useful for producing methylamines and having practical catalyst life and large selectivity for dimethylamine comprise crystalline silicoaluminophosphate molecular sieves which have a molar ratio of silicon atom to aluminum atom in the range of 0.01–0.30.

1 Claim, No Drawings

CATALYSTS FOR PRODUCING METHYLAMINES AND METHOD FOR MANUFACTURING THE SAME

This is a division of application Ser. No. 09/418,605, filed Oct. 15, 1999, now abandoned.

BACKGROUND OF THE INVENTION

1. Field of the Invention

The present invention relates to catalysts for producing methylamines and to method for manufacturing the catalysts. Methylamines, particularly, dimethylamine are important as starting materials for solvents represented by dimethylformamide, rubber products, pharmaceuticals and surfactants

2. Description of the Prior Art

Methylamines are produced usually from methanol and ammonia using solid acid catalysts such as silica-alumina, at a temperature around 400° C. Another known method comprises subjecting monomethylamine to a disproportionation reaction. The main product in the above methods for the production of methylamines is trimethylamine which has the least demand. However, dimethylamine is the most useful, and, therefore, methods for selectively producing dimethylamine have been demanded.

Methods for producing methylamines using zeolites which are more advantageous than conventional silica-alumina catalysts have also been proposed. For example, these methods use zeolites such as zeolite A (JP 56-69846 A), FU-1 (JP 54-148708 A), ZSM-5 (U.S.P. 4082805), ferrierite and erionite (JP 56-113747 A), ZK-5, Rho, chabazite and erionite (JP 61-254256 A), and mordenite (JP 56-46846 A, JP 58-49340 A, JP 59-210050 A, and JP 59-227841 A). In addition, there is a method for producing methylamines in an amount exceeding the thermodynamic equilibrium proportion, by using silicoaluminophosphates (JP 2-734 A).

The present inventors filed patent applications, on the basis of findings that silica-modified silicoaluminophosphates have greater activity and selectivity for dimethylamine than known zeolite catalysts and prior art silicoaluminophosphates (JP Application Nos. 9-197232, 9-360124 and 10-025832). However, the silica-modified silicoaluminophosphate catalysts have a problem of decrease in initial activity, so that a further improvement in life is demanded from a practical point of view.

SUMMARY OF THE INVENTION

The object of the present invention is to provide catalysts for producing methylamines which have a practical catalyst life and selectivity for dimethylamine and are free from the problem of decrease in activity encountered in the silicoaluminophosphate catalysts, and also methods for manufacturing the catalysts.

The inventors have found that crystalline silicoaluminophosphates having specific properties and compositional ratios which have never been referred to, in particular, those which are replaced with specific elements or those which are coated with the elements or oxides thereof have smaller decrease of initial activity with time and are effectively improved in catalyst life. As a result, a great improvement is obtained in life of silicoaluminophosphates having excellent initial activity and selectivity for dimethylamine as catalysts for producing methylamines.

The present invention relates to crystalline silicoaluminophosphate catalysts having improved life and being useful as catalysts for producing methylamines which are mainly composed of dimethylamine and produced by a reaction of methanol with ammonia, a reaction of methanol with monomethylamine or a disproportionation reaction of methylamines. The present invention relates also to methods for manufacturing the catalysts.

In more detail, the present invention includes the following aspects.

1) The present invention relates to a catalyst for producing methylamines which comprises a crystalline silicoaluminophosphate molecular sieve having a molar ratio of silicon atom to aluminum atom in the range of 0.01–0.30.

2) The present invention further relates to a method for manufacturing a catalyst for producing methylamines. It comprises mixing an aluminum compound, a phosphorus compound, a silicon compound, an amine or ammonium salt and water so that the molar ratio of them satisfies the following formula (1) when the aluminum compound, the phosphorus compound and the silicon compound are expressed by $Al_2O_3$, $P_2O_5$ and $SiO_2$, respectively, and then subjecting the mixture to a hydrothermal treatment:

$$Al_2O_3.(1\pm0.2)P_2O_5.(0.5\pm0.45)SiO_2.(1.5\pm0.45)Am.(75\pm25)H_2O \quad (1)$$

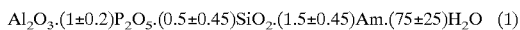

wherein Am denotes an amine or ammonium salt having 3 to 24 carbon atoms.

3) The present invention further relates to a method for producing methtylamines which comprises allowing methanol to react with ammonia in the presence of the crystalline silicoaluminophosphate molecular sieve mentioned in the above 1).

4) The present invention further relates to a method for producing methtylamines which comprises subjecting monomethylamine to a disproportionation reaction in the presence of the crystalline silicoaluminophosphate molecular sieve mentioned in the above 1).

DESCRIPTION OF THE PREFERRED EMBODIMENTS

For selective production of methylamines, especially, dimethylamine, preference for the molecular sieves is to have an effective micropore size ranging from 0.3 to 0.6 nm. According to the IUPAC structural code of zeolites and their analogous compounds, mention may be made of, for example, 8-membered ring-structural ABW, AEI, AFX, APC, ATN, ATT, ATV, AWW, CHA, DDR, EAB, ERI, GIS, JBW, KFI, LEV, LTA, MER, MON, PAU, PHI, RHO, RTE, RTH, and VNI; 9-membered ring-structural CHI, LOV, RSN, and VSV; 10-membered ring-structural DAC, EPI, FER, LAU, MEL, MFI, MFS, MTT, NES, TON, and WEI; and 12-membered ring-structural AFS, AFY, ATO, CAN, GME, MAZ, MEI, MTW, OFF, RON, and VET.

The present invention uses the crystalline silicoaluminophosphate molecular sieves (SAPO) having the above structures. The crystalline silicoaluminophosphate molecular sieves are products wherein a part of P or Al-P bond is replaced with Si by an isomorphic replacement, in a crystalline aluminum phosphate compound (ALPO) having a chemical composition of the following formula (2) which is represented by oxide mole ratios, excluding crystalline water and organic bases of structure directing agents (for example, JP 57-77015 A):

$$Al_2O_3.(1.0\pm0.2)P_2O_5 \quad (2).$$

Examples are SAPO-17, 18, 26, 31, 33, 34, 35, 37, 40, 41, 42, 44, 47 and 56, and especially preferred are SAPO-17, 18, 34, 35, 44, 47 and 56. Herein, the relationship between the SAPO numbers and their structures is mentioned, for example, in Encyclopedia of Inorganic Chemistry, Vol. 8, 4369 (1994). The IUPAC codes corresponding to SAPO-17, 18, 34, 35, 44, 47 and 56 are ERI, AEI, CHA, LEV, CHA, CHA, and AFX, respectively. The most preferred is SAPO-34 of chabazite structure.

These crystalline silicoaluminophosphate molecular sieves can be relatively readily manufactured using an aluminum compound, a phosphorus compound, a silicon compound, an amine or quaternary ammonium salt as a structure directing agent, and water.

As methods for manufacturing the crystalline silicoaluminophosphate molecular sieves, there are known methods as described in, for example, JP 59-35018 A and a method for manufacturing catalysts for producing methylamine as described in JP Application No. 9-197232 in which the sequence of addition of starting materials or the temperature range is specified. Anyone of the two methods can be employed. various products different in properties can be obtained depending on compositions or pHs of the starting mixtures, orders of addition of the starting materials, varieties of the structure directing agents, and/or conditions of hydrothermal synthesis.

However, in order to obtain those which have large activity and selectivity as catalysts for producing methylamine together with satisfactory catalyst life, it is most important that an atomic ratio of silicon to aluminum which constitute the crystalline silicoaluminophosphate molecular sieves falls within the range of 0.01–0.30. Furthermore, it is preferred that an average crystal grain size of the crystalline silicoaluminophosphate molecular sieves measured by a scanning electron microscope (SEM) is 5 μm or less, that the crystal has a cubic, rectangular parallelepipedic, spheroidal, hexagonal or prismatic form, and that both the size and the form of the crystal are uniform and regular. When the size of the crystal is 5 μm or less and the form of the crystal is as mentioned above, catalyst activity and selectivity are further improved and the catalyst life is further-prolonged.

Atomic ratio of silicon to aluminum should be samll. The larger the ratio, the shorter the catalyst life. However, as the ratio is smaller, crystallinity and form are so degraded that uniform crystals can hardly be obtained. Furthermore, size of crystals becomes uneven. Therefore, the ratio (Si/Al) is preferably in the range of 0.01–0.30, especially preferably in the range of 0.05–0.25. In the case of the above composition (Si/Al), atomic ratio of phosphorus to aluminum is preferably in the range of 0.7–0.9.

As the aluminum compounds used as the starting materials, preferred are pseudo-boehmite and aluminum alkoxides having 3 to 24 carbon atoms, such as aluminum isopropoxide. Pseudo-boehmite is especially preferred because use of it results in the longer crystal life though the reasons are not certain.

As the silicon compounds used as the starting materials, especially preferred are silica, silica sol, orthosilicic acid, and the like. The aluminum compounds and the silicon compounds usually contain alkali metals or alkaline earth metals as impurities. Such impurities usually facilitate an improvement in selectivity in reaction or initial activity as far as they are in a small amount. However, if they are contained in an amount exceeding a certain level, they sometimes have adverse influence on the catalyst life. Accordingly, the content of impurities should be 200 ppm or less.

As the phosphorus compounds used as the starting materials, especially preferred is orthophosphoric acid, but they are not limited thereto.

As the structure directing agents, preferred are amine or ammonium salts having 3 to 24 carbon atoms. Examples of them are trimethylamine, triethylamine, triethanolamine., isopropylamine, dibutylamine, dipentylamine, dihexylamine, piperidine, choline, morpholine, cyclohexylamine, 2-methylpyridine, 4-methylpyridine, tripropylamine, quinuclidine, N-methylcyclohexylamine, N,N-dimethylbenzylamine, N,N-dimethylethanolamine, N,N-25 diethylethanolamine, N,N-dimethylpiperazine, tetraethylammonium hydroxide, tetrapropylammonium hydroxide, and tetrabutylammonium hydroxide.

Metals and/or metal compounds can be added to the crystalline silicoaluminophosphate molecular sieves in order to improve methylamine catalysts in respect to activity, selectivity and catalyst life. As the metal species to be added, preferred are Li, Na, Be, Mg, Ca, Sr, Y, Ti, Zr, V, Nb, Cr, Mn, Fe, Ru, Co, Rh, Ir, Ni, Pd, Pt, Cu, Zn, B, Ga, In, Ge, and Sn. Ti, Y and Zr are especially preferred. That is, preferred are crystalline silicoaluminophosphate molecular sieves of H-type in which a part of the H-type is replaced with at least one metal selected from the species mentioned above. Alternatively, the same molecular sieves may be used, as long as they contain the metals or oxides of the metals. Especially preferred are the crystalline silicoaluminophosphate molecular sieves of H-type in which a part of the H-type is replaced with at least one metal selected from Ti, Y and Zr, and the same molecular sieves which contain titanium oxide, yttrium oxide or zirconium oxide.

One of manufacturing procedures for the crystalline silicoaluminophosphate molecular sieves containing the metals and/or the metal oxides is as follows. An aluminum compound, a phosphorus compound, a silicon compound, an amine or ammonium salt and water are mixed with at least one metal and/or a compound of the metal selected from Li, Na, Be, Mg, Ca, Sr, Y, Ti, Zr, v, Nb, Cr, Mn, Fe, Ru, Co, Rh, Ir, Ni, Pd, Pt, Cu, Zn, B, Ga, In, Ge and Sn so that the molar ratio satisfies the following formula (1). The aluminum compound, phosphorus compound and silicon compound are expressed by $Al_2O_3$, $P_2O_5$ and $SiO_2$, respectively. Then, the mixture is subjected to a hydrothermal treatment.

$$Al_2O_3.(1\pm0.2)P_2O_5.(0.5\pm0.45)\ SiO_2.(1.5\pm0.5)Am.(77\pm25) \quad (1)$$

wherein Am denotes an amine or ammonium salt having 3 to 24 carbon atoms.

The metal compounds to be added in this case are preferably in the form of water-soluble salts thereof such as nitrates, sulfates and hydrochlorides, Alternatively, metal alkoxides may be used. Furthermore, it is preferred that the metals are contained in an amount of 0.05–20% by weight in the silicoaluminophosphate.

The mixtures are subjected the hydrothermal treatment. The hydrothermal treatment of the starting mixture is carried out in the same manner regardless of whether addition of metals and/or metal compounds have been effected. That is, the treatment is effected until crystalline silicoaluminophosphate is obtained, preferably in a pressurized container having Teflon lining at a temperature of 100–250° C. under autogeneous pressure usually over a period of 1–200 hours. Then, the product thus obtained is subjected to filtration, decantation or centrifugal separation in order to separate crystals. In this case, it is preferred to effect repeated washing until the washing water is neutral. Thereafter, the product is dried by keeping it usually at 80–150° C. Moreover, the product is calcined in an oxidizing atmosphere such as air or in an air stream at a temperature of 350–700° C., preferably 500–600° C.

Alternatively, the addition of the metals and/or metal compounds to the crystalline silicoaluminophosphate molecular sieves may be carried out in such a manner that hydrogen in the crystalline silicoaluminophosphate molecular sieves of H-type is replaced with the metals of the metal compounds. The other approach is uniformly mixing the metals or metal oxides with the crystalline silicoaluminophosphate molecular sieves before shaping. The procedures for addition of the metals and/or metal oxides to the crystalline silicoaluminophosphate molecular sieves are not critical. No matter how the procedure may be, the product catalysts are in the form where a part of H-type of the catalysts is replaced with metal elements, or contain the metals or metal oxides.

The crystalline silicoaluminophosphate molecular sieves of the present invention can be suitably used, as they are, as catalysts for a reaction of methanol with ammonia, reaction of monomethylamine with methanol, and conversion reaction to dimethylamine according to a disproportionation reaction of monomethylamine or the like. Moreover, the crystalline silicoaluminophosphate molecular sieves of the present invention can be used for the other catalytic reactions. Furthermore, the present catalyst may be used as admixtures with other suitable molecular sieves. Suitable other molecular sieves to be admixed are, for example, aluminosilicates such as chabazite, mordenite, erionite, ferrierite, epistilbite, clinoptilolite, paulingite, phillipsite, levynite, zeolite-A, rho, ZK-5, FU-1, and ZSM-5. Furthermore, clay minerals such as kaolinite, halloysite, nacrite, montmorillonite, and illite may be optionally selected and added to the crystalline silicoaluminophosphate molecular sieves as binders.

When catalysts comprising the crystalline silicoaluminophosphate molecular sieves of the present invention are used for production of methylamines through a reaction of methanol with ammonia, production of methylamines through a reaction of methanol with monomethylamine, or production of methylamines through disproportionation reaction of monomethylamine, the reactions are conducted, preferably, in a flowing system on a gaseous fixed bed or fluidized bed, or in a system of supplying nitrogen or hydrogen during the flowing.

Reaction temperature in the production of methylamines or in the disproportionation reaction of monomethylamine is preferably 200–400° C., especially preferably 250–350° C. Reaction pressure is not critical. The reaction can be conducted under reduced pressure or under pressure, but preferably is conducted under pressure of 0.1–10 MPa. Naturally, the embodiments of the present invention are not limited to only the above descriptions.

EXAMPLES

The present invention will more fully be explained referring to the following examples and comparative examples. In these examples and comparative examples, reactions were conducted in a flowing reaction apparatus provided with material tanks, material feeding pumps, inert gas charging devices, reaction tubes (inner diameter of 13Ø, length of 300 mm, made of SUS 316L), sampling tanks, back pressure valves, etc. After 4 hours from the reaction reaching a steady state, the product sample was taken over 1 hour, and analyzed by a gas chromatography to obtain the composition distribution.

Catalyst Preparation Example 1

Zirconia-modified SAPO-34:

A mixture of 35% tetraethylammonium hydroxide (75.7 g) and pure water (42.3 g) was cooled to 5° C., and thereto was added aluminum isopropoxide (40.9 g) over a period of 3 minutes, followed by subjecting the mixture to high-speed stirring for 15 minutes. Then, thereto were added silica sol (9 g) and zirconia (1.2 g), and the mixture was subjected to high-speed stirring for 5 minutes until it became homogeneous. Furthermore, 85% phosphoric acid (23.1 g) was added, and the mixture was similarly stirred for 5 minutes, followed by milling for 1 hour. The resulting mixture was heated at 200° C. for 4 hours in an autoclave. The product was subjected to centrifugal separation and washing with water repeatedly 4 times, and then dried overnight at 110° C. Furthermore, the product was calcined at 600° C. for 4 hours in the air to obtain white crystal powder (22 g). XRD analysis of this powder gave a diffraction pattern corresponding to that of SAPO-34. The XRD pattern was sharp and showed a high crystallinity. The powder was observed by a scanning electron microscope to find that the crystal had a cubic form of about 1 $\mu$m and was highly uniform in both the size and the shape. Moreover, the powder was subjected to ICP analysis to find that the atomic ratio of silicon to aluminum was 0.20. This crystal was compression molded and then pulverized to obtain catalyst 1 comprising uniform particles of 1–2 mm.

Catalyst Preparation Example 2

SAPO-34:

A crystal of SAPO-34 which was high in crystallinity and in cubic form having a particle size of about 1 $\mu$m and having uniform size and shape was obtained in the same manner as in Catalyst Preparation Example 1, except that zirconia powder was not added. The atomic ratio of silicon to aluminum was 0.21. This crystal was compression molded and then pulverized to obtain catalyst 2 comprising uniform particles of 1–2 mm.

Catalyst Preparation Example 3

SAPO-34:

A mixture of 85% phosphoric acid (23.1 g) and pure water (75.3 g) was cooled to 5° C., and thereto was added diethanolamine as a structure directing agent (31.6 g) over a period of 10 minutes, followed by stirring for 2 hours. Then, thereto was added silica sol (12 g), and the mixture was subjected to high-speed stirring for 5 minutes until it became homogeneous. Furthermore, pseudo-boehmite (CATAPAL B manufactured by Condea Co., Ltd.)(14.4 g) was added as an aluminum source, followed by stirring for 2 hours. This mixture was heated at 200° C. for 60 hours in an autoclave. The product was subjected to centrifugal separation and washing with water, and then dried overnight at 110° C. Furthermore, the product was calcined at 600° C. for 4 hours in the air to obtain white crystalline powder (20 g). This crystal was SAPO-34 which had a cubic form of about 1 $\mu$m in particle size and was highly uniform in both the size and the shape. Moreover, the powder was subjected to ICP analysis to find that the atomic ratio of silicon to aluminum was 0.20. The resulting SAPO-34 was subjected to the same treatment as in Catalyst Preparation Example 1 to obtain catalyst 3.

Catalyst Preparation Example 4

SAPO-34:

SAPO-34 which had an atomic ratio of silicon to aluminum of 0.10 and was in cubic form having a particle size of about 1 $\mu$m and uniform in both the size and the shape was obtained in the same manner as in Catalyst Preparation Example 3, except that an amount of the silica sol was 6 g. The resulting SAPO-34 was subjected to the same treatment as in Catalyst Preparation Example 1 to obtain catalyst 4.

Catalyst Preparation Example 5

SAPO-34:

SAPO-34 which had an atomic ratio of silicon to aluminum of 0.15 and was in cubic form having a particle size of about 1 μm and uniform in both the size and the shape was obtained in the same manner as in Catalyst Preparation Example 3, except that an amount of the silica sol was 9. The resulting SAPO-34 was subjected to the same treatment as in Catalyst Preparation Example 1 to obtain catalyst 5.

Catalyst Preparation Example 6

SAPO-34:

SAPO-34 crystal was obtained in the same manner as in Catalyst Preparation Example 1, except that 35%-tetraethylammonium hydroxide was added after aluminum isopropoxide and phosphoric acid were added. The resulting crystal was in platy form having a particle size of about 1 μm. This was subjected to the same treatment and molding as in Catalyst Preparation Example 1 to obtain catalyst 6.

Catalyst Preparation Example 7

SAPO-5:

Catalyst 7 comprising SAPO-5 which was in cubic form having a particle size of 1 μm or less and uniform in both the size and the shape and having an atomic ratio of silicon to aluminum of 0.15 was obtained in the same manner as in Catalyst Preparation Example 3, except that an amount of diethanolamine was 41.2 g.

Catalyst Preparation Example 8

SAPO-44:

Catalyst 8 comprising SAPO-44 of chabazite structure was obtained in the same manner as in Catalyst Preparation Example 2, except that cyclohexylamine was used in place of the tetraethylammonium hydroxide as the structure directing agent. This catalyst was in cubic form and had a particle size of 20–100 μm.

Catalyst Preparation Example 9

SAPO-47:

Catalyst 9 comprising SAPO-47 of chabazite structure was obtained in the same manner as in Catalyst Preparation Example 2, except that methylbutylamine was used in place of the tetraethylammonium hydroxide as the structure directing agent. This catalyst was in cubic form and had a particle size of 40–100 μm.

Comparative Catalyst Preparation Example 1

SAPO-34:

Catalyst 10 comprising SAPO-34 which had an atomic ratio of silicon to aluminum of 0.35 was obtained in the same manner as in Catalyst Preparation Example 3, except that an amount of silica sol was 24.0 g.

Comparative Catalyst Preparation Example 2

SAPO-34:

Catalyst 11 comprising SAPO-34 which had an atomic ratio of silicon to aluminum of 0.004 was obtained in the same manner as in Catalyst Preparation Example 3, except that an amount of silica sol was 1.0 g.

Example 1

To a reaction tube filled with the catalyst 1 (4.5 g, 10 ml) was fed a mixture of methanol and ammonia (weight ratio, 1:1) at a rate of 15 g/h and a gas hourly space velocity (GHSV) of 1500 $h^{-1}$ to effect a reaction under a pressure of 2 MPa and a temperature of 330° C. The results of the initial reaction were shown below.

| Methanol conversion ratio: 98.8% | | |
|---|---|---|
| Selectivity: | Monomethylamine | 33 wt % |
| | Dimethylamine | 63 wt % |
| | Trimethylamine | 4 wt % |

After lapse of 150 hours, conversion ratio of methanol was 92.0% and no change was seen in amine selectivity. An accelerated life test was conducted with a GHSV of 2500 $h^{-1}$ using the same catalyst as above. As a result, the conversion ratio of methanol after lapse of 150 hours was 92.0%, and this test condition corresponded to 10 times accelerated life test as compared to that of the GHSV of 1500 $h^{-1}$.

Example 2

The same accelerated life test as in Example 1 was conducted using the catalyst 2 at a GHSV of 2500 $h^{-1}$. The initial methanol conversion ratio was 98.2%, and the conversion ratio after lapse of 150 hours was 89.0%.

Example 3

The same accelerated life test as in Example 1 was conducted using the catalyst 3 at a GHSV of 2500 $h^{-1}$. The methanol conversion ratio after lapse of 150 hours was 91.8%.

Example 4

The same accelerated life test as in Example 1 was conducted using the catalyst 4 at a GHSV of 2500 $h^{-1}$. The methanol conversion ratio after lapse of 150 hours was 93.2%.

Example 5

The same accelerated life test as in Example 1 was conducted using the catalyst 5 at a GHSV of 2500 $h^{-1}$. The methanol conversion ratio after lapse of 150 hours was 92.4%.

Example 6

The same accelerated life test as in Example 1 was conducted using the catalyst 6 at a GHSV of 2500 $h^{-1}$. The methanol conversion ratio after lapse of 150 hours was 79.5%.

Example 7

The same accelerated life test as in Example 1 was conducted using the catalyst 7 at a GHSV of 2500 $h^{-1}$. The methanol conversion ratio after lapse of 150 hours was 77.5%.

Example 8

The same accelerated life test as in Example 1 was methanol conversion ratio after lapse of 150 hours was 69.5%.

Example 9

The same accelerated life test as in Example 1 was conducted using the catalyst 9 at a GHSV of 2500 h$^{-1}$. The methanol conversion ratio after lapse of 150 hours was 72.0%.

Example 10

A dispersion of 5 wt % of stabilized zirconia in water was added to the catalyst 3 before subjected to molding. The mixture was well stirred until it became homogeneous, followed by drying overnight at 110° C. and then calcining at 600° C. for 4 hours to obtain a catalyst. The resulting catalyst was subjected to the same life test as in Example 1. The methanol conversion ratio after lapse of 150 hours as 94.5%.

Example 11

A dispersion of 5 wt % of chromium oxide powder in water was added to the catalyst 3 before subjected to molding. The mixture was well stirred until it became homogeneous, followed by drying overnight at 110° C. and then calcining at 600° C. for 4 hours to obtain a catalyst. The resulting catalyst was subjected to the same life test as in Example 1. The methanol conversion ratio after lapse of 150 hours was 92.6%.

Example 12

A dispersion of 5 wt % of tin oxide powder in water was added to the catalyst 3 before subjected to molding. The mixture was well stirred until it became homogeneous, followed by drying overnight at 110° C. and then calcining at 600° C. for 4 hours to obtain a catalyst. The resulting catalyst was subjected to the same life test as in Example 1. The methanol conversion ratio after lapse of 150 hours was 92.0%.

Example 13

A dispersion of 5 wt % of yttria oxide powder in water was added to the catalyst 3 before subjected to molding. The mixture was well stirred until it became homogeneous, followed by drying overnight at 110° C. and then calcining at 600° C. for 4 hours to obtain a catalyst. The resulting catalyst was subjected to the same life test as in Example 1. The methanol conversion ratio after lapse of 150 hours was 92.0%.

Example 14

A dispersion of 5 wt % of indium oxide powder in water was added to the catalyst 3 before subjected to molding. The mixture was well stirred until it became homogeneous, followed by drying overnight at 110° C. and then calcining at 600° C. for 4 hours to obtain a catalyst. The resulting catalyst was subjected to the same life test as in Example 1. The methanol conversion ratio after lapse of 150 hours was 92.0%.

Comparative Example 1

The same accelerated life test as in Example 1 was conducted using the catalyst 10 at a GHSV of 2500 h$^{-1}$. The methanol conversion ratio after lapse of 150 hours was 68.5%.

Comparative Example 2

The same accelerated catalyst life test as in Example 1 was conducted using the catalyst 11 at a GHSV of 2500 h$^{-1}$. The methanol conversion ratio after lapse of 150 hours was 69.0%.

Example 15

To a reaction tube filled with the catalyst 1 (2.0 g, 4.0 ml) was fed monomethylamine at a GHSV of 2500 h$^{-1}$ under a reaction pressure of 2 MPa and a temperature of 350° C. to conduct an accelerated life test. The results of disproportionation reaction to produce ammonia and dimethylamine from monomethylamine were shown below.

| Monomethylamine conversion ratio: 83.1% | | |
|---|---|---|
| Selectivity: | Dimethylamine | 97 wt % |
|  | Trimethylamine | 3 wt % |

The conversion ratio of monomethylamine after lapse of 150 hours was 82.8%.

Example 16

The accelerated life test in disproportionation of monomethylamine was conducted in the same manner as in Example 15 using the catalyst 2 at a GHSV of 2500 h$^{-1}$. The monomethylamine conversion ratio after lapse of 150 hours was 82.2%.

The results of the reactions of methanol with ammonia and the disproportionation reactions of monomethylamine in Examples of the present invention and Comparative Examples are shown in Table 1.

TABLE 1

| Catalysts | | Si/Al | Particle size μm | Shapes | Preparation methods* | Conversion ratios at life test | |
|---|---|---|---|---|---|---|---|
| | | | | | | Initial % | 150 h % |
| (Accelerated life test) | | | | | | | |
| Ex. 1 | 1 (ZrSAPO – 34) | 0.20 | 3 | cubic | A | 98.8 | 92.0 |
| Ex. 2 | 2 (SAPO – 34) | 0.21 | 1 | cubic | A | 98.2 | 89.0 |
| Ex. 3 | 3 (SAPO – 34) | 0.20 | 1 | cubic | B | 98.6 | 91.8 |
| Ex. 4 | 4 (SAPO – 34) | 0.10 | 1 | cubic | B | 97.8 | 93.2 |
| Ex. 5 | 5 (SAPO – 34) | 0.15 | 1 | cubic | B | 98.2 | 92.4 |
| Ex. 6 | 6 (SAPO – 34) | 0.16 | 1 | platy | A | 94.3 | 79.5 |
| Ex. 7 | 7 (SAPO – 5) | 0.15 | 1 | cubic | A | 82.4 | 77.5 |

TABLE 1-continued

| Catalysts | | Si/Al | Particle size μm | Shapes | Preparation methods* | Conversion ratios at life test | |
|---|---|---|---|---|---|---|---|
| | | | | | | Initial % | 150 h % |
| Ex. 8 | 8 (SAPO – 44) | 0.30 | 20–100 | cubic | B | 79.2 | 69.5 |
| Ex. 9 | 9 (SAPO – 47) | 0.29 | 40–100 | cubic | B | 82.0 | 72.0 |
| Ex. 10 | 3a (Zr + 3) | 0.20 | 1 | cubic | B | 98.8 | 94.5 |
| Ex. 11 | 3b (Cr + 3) | 0.20 | 1 | cubic | B | 98.8 | 92.6 |
| Ex. 12 | 3c (Sn + 3) | 0.20 | 1 | cubic | B | 98.8 | 92.0 |
| Ex. 13 | 3d (Y + 3) | 0.20 | 1 | cubic | B | 98.8 | 92.0 |
| Ex. 14 | 3e (In + 3) | 0.20 | 1 | cubic | B | 98.8 | 92.0 |
| Comp. Ex. 1 | 10 (SAPO – 34) | 0.35 | 1 | cubic | B | 92.2 | 68.5 |
| Comp. Ex. 2 (Disporportionation reaction) | 11 (SAPO – 34) | 0.004 | 1 | cubic | B | 90.6 | 69.0 |
| Ex. 15 | 1 (ZrSAPO – 34) | 0.20 | 1 | cubic | A | 83.1 | 82.8 |
| Ex. 16 | 2 (SAPO – 34) | 0.20 | 1 | cubic | A | 82.8 | 82.2 |

Notes
1. Reaction conditions: Temperature 330° C.; pressure 2MPa; GHSV 2500 h$^{-1}$
2. Preparation methods*: A (aluminum source: aluminum isopropoxide)  B (aluminum source: aluminum pseudo-boehmite)

The results of Examples and Comparative Examples show that the catalysts of the present invention produce only a small amount of trimethylamine which has little demand in the production of methylamines through the reaction of methanol with ammonia or the production of dimethylamine through a disproportionation reaction of methylamines. The present catalysts have a prolonged life than conventional catalysts. Therefore, the catalysts and the manufacturing methods thereof provided by the present invention are useful for selective production of dimethylamine, and the present invention has very large industrial values.

What is claimed is:

1. A method for producing methylamines which comprises carrying out a disproportionation reaction of monomethylamine in the presence of a crystalline silicoaluminophosphate molecular sieve that has a cubic, rectangular parallelepipedic, spheroidal, hexagonal or prismatic form, wherein said molecular sieve has a molar ratio of silicon atoms to aluminum atoms in the range of 0.01 to 0.30.

* * * * *